United States Patent [19]

Nikolson et al.

[11] Patent Number: 4,466,969
[45] Date of Patent: Aug. 21, 1984

[54] 7-OXOPROSTACYCLIN DERIVATIVES AND THEIR USE AS HYPOTENSIVES AND BRONCHODILATORS

[75] Inventors: Robert C. Nikolson; Helmut Vorbrüggen; Jorge Casals-Stenzel; Gerda Mannesmann, all of Berlin, Fed. Rep. of Germany

[73] Assignee: Schering Aktiengesellschaft, Berlin and Bergkamen, Fed. Rep. of Germany

[21] Appl. No.: 385,414

[22] PCT Filed: Sep. 17, 1981

[86] PCT No.: PCT/EP81/00148
§ 371 Date: May 17, 1982
§ 102(e) Date: May 17, 1982

[87] PCT Pub. No.: WO82/01002
PCT Pub. Date: Apr. 1, 1982

[30] Foreign Application Priority Data

Sep. 18, 1980 [DE] Fed. Rep. of Germany ....... 3035454

[51] Int. Cl.³ ................. A61K 31/557; C07D 307/935
[52] U.S. Cl. .................................. 424/263; 424/274; 424/275; 424/285; 546/269; 548/525; 549/60; 549/415; 549/465
[58] Field of Search ......................... 549/465, 415, 60; 542/426; 424/285, 274, 275, 263; 546/269; 548/525

[56] References Cited
U.S. PATENT DOCUMENTS 4,330,553 5/1982 Simonidesz et al. ................ 549/465

Primary Examiner—Henry R. Jiles
Assistant Examiner—Bernard Dentz
Attorney, Agent, or Firm—Millen & White

[57] ABSTRACT

Prostacyclin, although having a useful dilating effect on blood vessels, is not sufficiently stable to ensure successful use as a hypotensive agent.

A 7-oxo prostacyclin derivative of the general formula

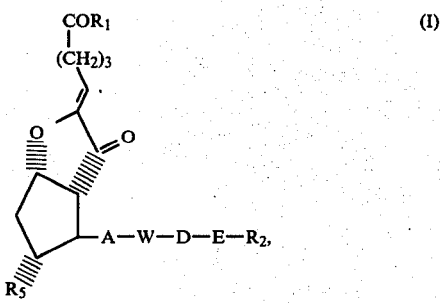

in which
$R_1$ represents the radical $OR_3$ wherein
$R_3$ represents hydrogen, a straight-chain or branched optionally substituted, $(C_1-C_{10})$alkyl, optionally substituted aryl, optionally substituted cycloalkyl, optionally substituted heterocyclic,
or
$R_1$ represents the radical $NHR_4$ wherein
$R_4$ represents hydrogen, or a group derived from an unsaturated or saturated, unsubstituted or substituted, $(C_1-C_{15})$organic carboxylic or sulphonic acid,
A represents $-CH_2-CH_2-$, cis$-CH=CH-$ or trans$-CH=CH-$,
W represents

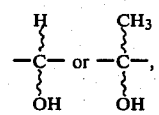

either having a free or functionally modified hydroxy group which may be in the α- or β-position,
D and E together represent a direct bond, or
D represents a straight-chain or branched, unsaturated or saturated, optionally substituted $(C_1-C_{10})$alkylene, and
E represents oxygen or a direct bond,
$R_2$ represents a straight-chain or branched optionally substituted, $(C_1-C_{10})$alkyl, a straight-chain or branched optionally substituted, $(C_2-C_{10})$alkenyl, or, where D and E together represent a direct bond, a straight-chain or branched optionally substituted $(C_2-C_6)$alkynyl,
and
$R_5$ represents a free or functionally modified hydroxy group,
has proved to have not only a hypotensive and bronchodilative action, for example, but also an increased stability over prostacyclin. Advantages in medicinal use over other prostaglandins have also been found.

29 Claims, No Drawings

7-OXOPROSTACYCLIN DERIVATIVES AND THEIR USE AS HYPOTENSIVES AND BRONCHODILATORS

The invention relates to prostacyclin derivatives, a process for their manufacture and their use as medicaments.

Prostacyclin (PGI$_2$), one of the main factors in blood platelet aggregation, has a dilating effect on various blood vessels (Science 196, 1072) and could therefore come into consideration as an agent for reducing blood pressure. PGI$_2$ does not, however, possess the stability necessary for use as a medicament. For example, its half life at physiological pH values and at room temperature is only a few minutes.

We have now found that the introduction of an oxo group in the 7-position of the prostacyclin results in stabilisation of the prostacyclin molecule whilst retaining the pharmacological range of action and the duration of action of these prostacyclins is distinctly prolonged.

The compounds according to the present invention have a hypotensive and bronchodilative action. They are also suitable for inhibiting thrombocyte aggregation, vasoconstriction and gastric acid secretion.

The present invention provides a 7-oxoprostacyclin of the general formula

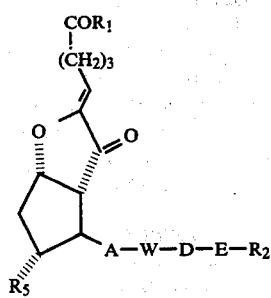

(I)

in which
R$_1$ represents the radical OR$_3$ wherein
  R$_3$ represents a hydrogen atom, a straight-chain or branched-chain, unsubstituted or substituted, alkyl radical having from 1 to 10 carbon atoms, an unsubstituted or substituted aryl radical, an unsubstituted or substituted cycloalkyl radical, or an unsubstituted or substituted heterocyclic radical or
R$_1$ represents the radical NHR$_4$ wherein
  R$_4$ represents a hydrogen atom, or a group derived from an unsaturated or saturated, unsubstituted or substituted, organic carboxylic or sulphonic acid having from 1 to 15 carbon atoms,
A represents a —CH$_2$—CH$_2$—, cis —CH=CH— or trans —CH=CH— group,
W represents

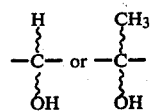

group, the hydroxy group of which may be free or functionally modified and may be in the α- or β-position, D and E together represent a direct bond, or
D represents a straight-chain or branched-chain, unsaturated or saturated, unsubstituted or substituted alkylene radical having from 1 to 10 carbon atoms, and
E represents an oxygen atom or a direct bond,
R$_2$ represents a straight-chain or branched-chain, unsubstituted or substituted, alkyl radical having from 1 to 10 carbon atoms, a straight-chain or branched-chain, unsubstituted or substituted, alkenyl radical having from 2 to 10 carbon atoms, or, where D and E together represent a direct bond, a straight-chain or branched-chain, unsubstituted or substituted, alkynyl radical having from 2 to 6 carbon atoms,
and
R$_5$ represents a free or functionally modified hydroxy group.

As alkyl groups represented by R$_3$, there come into consideration straight-chain or branched alkyl groups having from 1 to 10 carbon atoms, such as, for example, methyl, ethyl, propyl, butyl, isobutyl, tert.-butyl, pentyl, neopentyl, heptyl, hexyl or decyl radicals. The alkyl groups R$_3$ may optionally be substituted by one or more of the same or different substituents selected from halogen atoms, alkoxy radicals having from 1 to 4 carbon atoms, optionally substituted aryl groups, dialkylamines and trialkylammonium radicals each having from 1 to 4 carbon atoms in each alkyl radical. Those alkyl groups which are mono-substituted are preferred. Examples of substituents that may be mentioned are fluorine, chlorine and bromine atoms and phenyl, dimethylamine, methoxy and ethoxy radicals. As preferred alkyl groups R$_3$ are those having from 1 to 4 carbon atoms, such as, for example, methyl, ethyl, propyl, dimethylaminopropyl, isobutyl and butyl radicals.

As aryl groups represented by R$_3$, there come into consideration both substituted and unsubstituted aryl groups, such as, for example, phenyl, 1-naphthyl and 2-naphthyl radicals which may each be substituted by from 1 to 3 halogen atoms, a phenyl group, from 1 to 3 alkyl radicals each having from 1 to 4 carbon atoms, a chloromethyl, fluoromethyl, trifluoromethyl, carboxy or hydroxy radical or an alkoxy radical having from 1 to 4 carbon atoms. Preferably, the substituents are in the 3- and 4-positions on the phenyl ring, for example fluorine, chlorine, alkoxy or trifluoromethyl radicals or, in the 4-position, hydroxy radicals.

A cycloalkyl group represented by R$_3$ may contain from 4 to 10, preferably 5 and 6, carbon atoms in the ring. The rings may be substituted by alkyl radicals having from 1 to 4 carbon atoms. There may be mentioned, for example, cyclopentyl, cyclohexyl, methylcyclohexyl and adamantyl radicals.

As heterocyclic groups represented by R$_3$, there come into consideration 5- and 6-membered heterocycles, among which those having a hetero atom, such as, for example, nitrogen, oxygen or sulphur, are especially preferred. There may be mentioned, for example: inter alia, 2-furyl, 2-thienyl, 2-pyridyl, 3-pyridyl, 4-pyridyl.

As the acid radical represented by R$_4$, there come into consideration physiologically tolerable acid radicals. Preferred acids are organic carboxylic acids and sulphonic acids having from 1 to 15 carbon atoms belonging to the aliphatic, cycloaliphatic, aromatic, aromaticaliphatic and heterocyclic series. These acids may be saturated, unsaturated and/or polybasic and/or substituted in the usual manner. Examples of substituents that may be mentioned are alkyl, hydroxy, alkoxy, oxo or amino radicals or halogen atoms.

The following carboxylic acids may be mentioned by way of example: formic acid, acetic acid, propionic acid, butyric acid, isobutyric acid, valeric acid, isovaleric acid, caproic acid, oenanthic acid, caprylic acid, pelargonic acid, capric acid, undecylic acid, lauric acid, tridecylic acid, myristic acid, pentadecylic acid, trimethylacetic acid, diethylacetic acid, tert.-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and tri-chloroacetic acid, aminoacetic acid, diethylaminoacetic acid, piperidinoacetic acid, morpholinoacetic acid, lactic acid, succinic acid, adipic acid, benzoic acid or benzoic acid substituted by halogen or trifluoromethyl, hydroxy, alkoxy or carboxy groups, nicotinic acid, isonicotinic acid, furan-2-carboxylic acid, cyclopentylpropionic acid. Especially preferred acyl radicals are those having up to 10 carbon atoms. Suitable sulphonic acids are, for example, methanesulphonic acid, ethanesulphonic acid, isopropanesulphonic acid, β-chloroethanesulphonic acid, butanesulphonic acid, cyclopentanesulphonic acid, cyclohexanesulphonic acid, benzenesulphonic acid, p-toluenesulphonic acid, p-chlorobenzenesulphonic acid, N,N-dimethylaminosulphonic acid, N,N-diethylaminosulphonic acid, N,N-bis(β-chloroethyl)-aminosulphonic acid, N,N-diisobutylaminosulphonic acid, N,N-dibutylaminosulphonic acid and pyrrolidin-1-yl, piperidino-, piperazin-1-yl-, N-methylpiperazin-1-yl- and morpholino-sulphonic acid.

The hydroxy groups represented by $R_5$ and those in W may be functionally modified, for example by etherification or esterification, it being possible for the free or modified hydroxy groups in W to be in the α- or β-position, free hydroxy groups being preferred. The ether and acyl radicals that come into consideration are those known to the main skilled in the art. Ether radicals that can readily be split off are preferred, such as, for example, the tetrahydropyranyl, tetrahydrofuranyl, α-ethoxyethyl, trimethylsilyl, dimethyl-tert.-butylsilyl and tribenzylsilyl radical. Suitable acyl radicals are $(C_1-C_4)$-alkanoyl radicals, such as, for example, acetyl, propionyl, butyryl or benzoyl radicals.

As alkyl and alkenyl groups represented by $R_2$, there come into consideration straight-chain and branched alkyl radicals having from 1 to 10, especially 1 to 6, carbon atoms and straight-chain and branched alkenyl radicals having from 2 to 10, especially 2 to 6, carbon atoms, each of which may optionally be substituted by optionally substituted aryl radicals, alkyl radicals having from 1 to 4 carbon atoms or halogen atoms. There may be mentioned, for example, methyl, ethyl, propyl, butyl, isobutyl, tert.-butyl, pentyl, hexyl, heptyl, oxtyl, butenyl, isobutenyl, propenyl, pentenyl, hexenyl and benzyl radicals and, where D and E together represent a direct bond, alkynyl radicals having from 2 to 6 carbon atoms optionally substituted in the 1-position by fluorine or $(C_1-C_4)$-alkyl radicals. As alkynyl radicals, there come into consideration: ethynyl, propyn-1-yl, propyn-2-yl, 1-methylpropyn-2-yl, 1-fluoropropyn-2-yl, 1-ethylpropyn-2-yl, 1-fluorobutyn-2-yl, butyn-2-yl, butyn-3-yl, 1-methylbutyn-3-yl, 1-methylpentyn-3-yl, 1-fluoropentyn-3-yl, 1-methylpentyn-2-yl, 1-fluoropentyn-2-yl, 1-methylpentyn-4-yl, 1-fluoropentyn-4-yl, hexyn-1-yl, 1-methylhexyn-2-yl, 1-fluorohexyn-2-yl, 1-methylhexyn-3-yl, 1-methylhexyn-4-yl, hexyn-3-yl, etc.

For halogen as a substituent of the alkyl and alkenyl groups represented by $R_2$, there come into consideration bromine, chlorine and fluorine. Chlorine and fluorine are preferred. Among the branched alkyl radicals $R_2$ there are preferred especially those which, having regard to the radicals D and E, produce a 17-$(C_1-C_4)$-alkyl branch in the prostacyclin molecule, for example when D and E are to represent a direct bond, isobutyl, 2-methylpentyl, 2-ethylpentyl, 2-butylpentyl, etc. may be used.

As an alkylene groups represented by D, there come into consideration straight-chain or branched-chain alkylene radicals that may contain a double bond, but are preferably saturated, having from 1 to 10, especially 1 to 5, carbon atoms which may optionally be substituted, especially in the 1- or 2-position, by fluorine atoms or $(C_1-C_4)$-alkyl radicals. There may be mentioned, for example: methylene, fluoromethylene, ethylene, 1,2-propylene, ethylethylene, trimethylene, tetramethylene, pentamethylene, 1-methyltetramethylene, 1-methyltrimethylene, 2-methyltrimethylene, 2-methyltetramethylene. If a double bond is present, it is usually situated in the alkylene radicals having from 4 to 10 carbon atoms in the 2- or 3-position.

For salt formation with the free acids (i.e. when $R_3=H$), inorganic and organic bases are suitable, such as those known to the man skilled in the art for the formation of physiologically tolerable salts.

There may be mentioned as salt-forming agents, for example: alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl)methylamine, etc.

The present invention further provides a process for the preparation of a 7-oxoprostacyclin of the invention, or a salt thereof, which comprises reacting a compound of the general formula

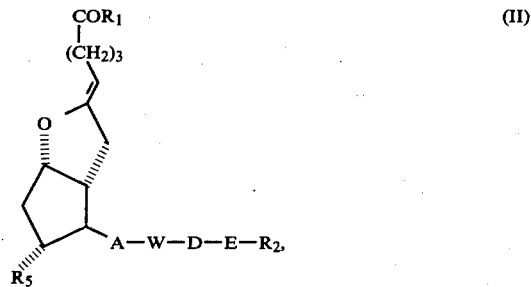

in which $R_1$, $R_2$, $R_5$, A, W, D and E have the meanings given above, with selenium dioxide and, if appropriate and desired, converting an acid into a salt, a salt into an acid or a salt into another salt.

The reaction of a compound of the general formula II with selenium dioxide may be carried out at temperatures of from 20° to 140° C., preferably at from 50° to 120° C., in an organic solvent, preferably dioxan or tert.-butanol, for from 0.5 to 10 hours under inert gas (such as, for example, nitrogen or argon) and while stirring optionally with the addition of an amine base, such as pyridine or hexamethyldisilazane. The reaction of a compound of the general formula II with selenium dioxide may be carried out by methods known to the man skilled in the art.

Hydrolysis of the 7-oxoprostacyclin esters may be carried out according to methods known to the man skilled in the art, for example with basic catalysts. The introduction of the ester group in which $R_3$ represents an alkyl group having from 1 to 10 carbon atoms may also be effected according to methods known to the man skilled in the art. The carboxy compounds may be reacted in a manner known per se, for example with diazohydrocarbons. Esterification with diazohydrocarbons may be carried out, for example, by mixing a solution of the diazohydrocarbon in an inert solvent, preferably in diethyl ether, with the carboxy compound in the same or in a different solvent, such as, for example, methylene chloride. When the reaction is complete after 1 to 30 minutes, the solvent is removed and the ester is purified in customary manner. Diazoalkanes are either known or can be manufactured according to known methods [Org. Reactions Vol. 8, pages 389–394 (1954)].

The introduction of the ester group $OR_3$ for $R_1$, in which $R_3$ represents a substituted or unsubstituted aryl group, may be carried out according to methods known to the man skilled in the art. For example, the carboxy compounds may be reacted with the corresponding arylhydroxy compounds with dicyclohexyl carbodiimide in the presence of a suitable base, for example pyridine or triethylamine, in an inert solvent. Suitable solvents are methylene chloride, ethylene chloride, chloroform, ethyl acetate, tetrahydrofuran, and preferably chloroform. The reaction may be carried out at temperatures between $-30°$ C. and $50°$ C., preferably at $10°$ C.

The 7-oxoprostacyclin derivatives of the general formula I in which $R_3$ represents a hydrogen atom can be converted into salts with suitable neutralising amounts of an inorganic base. For example, a solid inorganic salt may be obtained on dissolving the PG acids in water containing a stoichiometric amount of the base, after evaporating off the water or after adding a water-miscible solvent, for example alcohol or acetone.

For the manufacture of an amine salt, which may be carried out in customary manner, the PG acid is, for example, dissolved in a suitable solvent, for example ethanol, acetone, acetonitrile, diethyl ether or benzene, and at least the stoichiometric amount of the amine is added to that solution. In this case, the salt is usually obtained in solid form or is isolated in customary manner after evaporation of the solvent.

The functional modification of the free OH groups may be carried out according to methods known to the man skilled in the art. For the introduction of ether protecting groups, for example, the reaction may be carried out with dihydropyran in methylene chloride, benzene or chloroform using an acid catalyst, such as, for example, $POCl_3$, p-toluenesulphonic acid or anhydrous mineral acids. Dihydropyran is used in excess, preferably in 2 times to 10 times the amount theoretically required. The reaction is usually complete after 15 to 30 minutes at from $0°$ C. to $30°$ C.

Acyl protecting groups may be introduced by reacting a compound of the general formula I, in a manner known per se, with a carboxylic acid derivative, such as, for example, inter alia an acid chloride or acid anhydride, in the presence of a tertiary amine base, such as, for example, pyridine and dimethylaminopyridine.

Freeing of a functionally modified OH group to form compounds of the general formula I may be carried out according to known methods. For example, splitting off of ether protecting groups may be carried out in an aqueous solution of an organic acid, such as, for example, inter alia, acetic acid or propionic acid, or in an aqueous solution of an inorganic acid, such as, for example, hydrochloric acid. To improve solubility, a water-miscible inert organic solvent is advantageously added. Suitable organic solvents are, for example, alcohols, such as methanol and ethanol, and ethers, such as dimethoxyethane, dioxan and tetrahydrofuran. Tetrahydrofuran is preferably used. Splitting off is preferably carried out at temperatures of between $20°$ C. and $80°$ C.

Splitting off of the silyl ether protecting groups may be carried out, for example, with tetrabutylammonium fluoride or with potassium fluoride in the presence of a Crown ether. Suitable solvents are, for example, tetrahydrofuran, diethyl ether, dioxan, methylene chloride, etc. Splitting off is preferably carried out at a temperature in the range of from $0°$ C. to $80°$ C.

Hydrolysis of the acyl groups may be carried out, for example, with alkali metal or alkaline earth metal carbonates or hydroxides in an alcohol or an aqueous solution of an alcohol. As alcohols there come into consideration aliphatic alcohols, such as, for example, methanol, ethanol and butanol, preferably methanol. As alkali metal carbonates and hydroxides there may be mentioned sodium and potassium salts, but potassium salts are preferred. As alkaline earth metal carbonates and hydroxides there are suitable, for example, calcium carbonate, calcium hydroxide and barium carbonate. The reaction may be carried out at a temperature in the range of from $-10°$ C. to $70°$ C., preferably at $25°$ C.

The reaction of the compound of the general formula I in which $R_3$ represents a hydrogen atom, with an isocyanate of the general formula

$$R_4-N=C=O \qquad (V)$$

in which $R_4$ has the meaning given above, may be carried out optionally with the addition of a tertiary amine, such as, for example, triethylamine or pyridine. The reaction can be carried out without solvent or in an inert solvent, preferably acetonitrile, tetrahydrofuran, acetone, dimethylacetamide, methylene chloride, diethyl ether, benzene, toluene or dimethyl sulphoxide, at temperatures above or below room temperature, for example in the range of from $-80°$ C. and $100°$ C., preferably from $0°$ C. to $30°$ C.

The compounds of the general formula II used as starting material may be prepared, for example, by reacting, in a manner known per se, a known prostaglandin F-derivative of the general formula

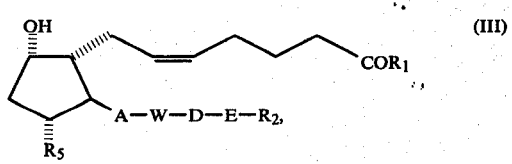

with iodine in the presence of an alkali metal bicarbonate or alkali metal carbonate to form a compound of the general formula

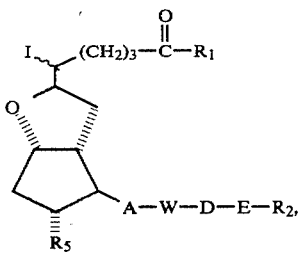

(IV)

[J. Tömöskäzi et al., Tetrahedron Letters, 2627 (1977)].

Subsequently, free hydroxy groups may optionally be protected by esterification, etherification or silylation. Depending on the desired meaning of A or other radicals in the compounds of the general formula I, a double bond in a compound of the general formula IV may optionally be hydrogenated or, optionally, a carboxy group may be esterified or a carboxy group may be reacted with a compound of the general formula V.

The reaction of a compound of the general formula IV to give a compound of the general formula II may be carried out, for example, with 1,5-diazabicyclo[3.4.0]-5-nonene (DBN) or 1,5-diazabicyclo[5.4.0]-5-undecene (DBU) in an inert solvent, such as benzene, toluene, and tetrahydrofuran or with sodium methoxide in methanol. The splitting off of a hydrogen halide may be carried out at a temperature in the range of from 0° C. to 120° C., preferably from 20° to 60° C.

If, finally, end products that contain free hydroxy groups in the prostane radical are desired, the starting materials advantageously used are those in which the hydroxy groups are protected intermediately by ether or acyl radicals that may preferably be split off readily.

The compounds of this invention have a hypotensive and bronchodilative action. They are also suitable for the inhibition of thrombocyte aggregation. Consequently, the prostacyclin derivatives of the general formula I are valuable pharmaceutically active substances. Furthermore, compared with corresponding prostaglandins, whilst having a similar spectrum of action, they exhibit higher specificity and, above all, substantially longer activity. In comparison with $PGI_2$ they are distinguished by greater stability. The high tissue specificity of the prostaglandins of the invention is apparent in studies on smooth muscular organs, such as, for example, the ileum of guinea pigs or the isolated trachea of rabbits, where a substantially lower stimulation is to be observed than in the case of administering natural prostaglandins of the E, A or F type.

The prostaglandin analogues of the invention possess properties typical of prostacyclins, such as, for example, reduction of peripheral arterial and coronary vascular resistance, inhibition of thrombocyte aggregation and breaking up of platelet thrombi, myocardial cytoprotection and, therewith, lowering of the systemic blood pressure without simultaneously reducing cardiac output and coronary blood flow; treatment of stroke, prophylaxis and therapy of coronary heart diseases, coronary thrombosis, cardiac infarct, peripheral artery diseases, arteriosclerosis and thrombosis, prophylaxis and therapy of ischaemic attacks of the CNS system, therapy of shock, inhibition of bronchoconstriction, inhibition of gastric acid secretion and cytoprotection of the gastric and intestinal mucosa and cytoprotection in the liver and pancreas; antiallergic properties, reduction of pulmonary vascular resistance and of pulmonary blood pressure, stimulation of the blood flow through the kidneys, use instead of heparin or as adjuvant in the dialysis of haemofiltration, preservation of blood plasma supplies, especially blood platelet supplies, inhibition of labour pains, treatment of toxaemia in pregnancy, increase of cerebral blood flow etc.. In addition, the prostaglandin analogues of the invention have antiproliferative properties. The prostacyclins of the invention can also be used in combination, for example with β-blockers or diuretics. The dosage of the compounds is usually from 1 to 1500 μg/kg/day when administered to human patients. The unit dose for the pharmaceutically acceptable carrier is generally from 0.01 to 100 mg.

In the case of intravenous injection to conscious hypertonic rats in doses of 5, 20 and 100 μg/kg body weight, the compounds of the invention have been found to exhibit a more strongly hypotensive and longer lasting action than $PGE_2$ and $PGA_2$ without causing diarrhoea like $PGE_2$ or cardiac arrhythmia like $PGA_2$.

In the case of intravenous injection to narcotised rabbits, the compounds of the invention exhibit, in comparison with $PGE_2$ and $PGA_2$, a stronger and considerably longer lasting reduction in blood pressure without other smooth muscular organs or organ functions being affected.

For parenteral administration, sterile, injectable, aqueous or oily solutions are used. For oral administration, for example tablets, dragées or capsules are suitable.

Accordingly, the present invention also provides a pharmaceutical preparation which comprises a compound of the general formula I, or a physiologically tolerable salt thereof, in admixture or conjunction with a pharmaceutically suitable carrier.

The active substances of the invention should serve in conjunction with the adjuncts known and customary in galenical pharmacy, for example for the manufacture of hypotensors.

The following Examples illustrate the invention.

Example 1

11,15-bis(O-acetyl)-16-fluoro-7-oxoprostacyclin methyl ester 45 mg of selenium dioxide are added to a solution of 470 mg of 16-fluoroprostacyclin-11,15-diacetate methyl ester in 10 ml of absolute dioxan and the mixture is heated at 100° C. under argon for 1.5 hours. The solution is stirred into ice-water and the mixture is extracted alternately with ether and ethyl acetate. The organic phases are combined, washed with water, dried over magnesium sulphate and concentrated. 228 mg of crude product are obtained which is purified on preparative thin-layer plates (in hexane/ethyl acetate/triethylamine 7:3:0.5 as eluant). 161 mg of the title compound are obtained in the form of an oil.

IR: 2940, 1740, 1710, 1660, 1460, 1360, 1250/cm.

The starting material for Example 1 is prepared as follows:

(1a) 16-fluoroprostaglandin $F_{2\alpha}$-methyl ester (German Offenlegungsschrift 23 20 368)

A diazomethane solution is added at 0° C. to a solution of 840 mg of 16-fluoroprostaglandin $F_{2\alpha}$ in 30 ml of diethyl ether until the yellow colour of the reaction solution is constant. Excess diazomethane is removed by the dropwise addition of glacial acetic acid and the colourless solution is concentrated in vacuo. The crude product is chromatographed on silica gel by gradient elution in methylene chloride/acetone mixture. B 790 mg of the title compound are obtained.

(1b) 5,6-dihydro-16-fluoro-5-iodoprostacyclin methyl ester 46 ml of water and 2.86 g of sodium bicarbonate are added to a solution of 770 mg of the methyl ester prepared in EXAMPLE (1a) in 28 ml of ether. The mixture is cooled to 0° C. and 40 ml of 2.5% iodine solution in ether are added over a period of 30 minutes. After 4 hours, ether was added to the reaction mixture, and the aqueous phase was separated off and extracted with ether. The combined ether phases are washed in succession with 5% thiosulphate solution and brine. The ether solution is dried over magnesium sulphate and concentrated. The crude product is filtered over silica gel in methylene chloride/20% acetone. 1.04 g of the title compound is obtained.

(1c) 5,6-dihydro-16-fluoro-5-iodoprostacyclin-11,15-diacetate methyl ester 1.04 g of the diol prepared according to Example (1b) are dissolved in 5.7 ml of pyridine after 1.50 ml of acetic anhydride and the mixture is left to stand at room temperature for 18 hours. The solution is extensively concentrated in vacuo and the residue is filtered over silica gel in pentane/ether (7:3). 1.17 g of the title compound are obtained in the form of a colourless oil.

IR: 2960, 2950, 2860, 2730, 1245, 975/cm.

(1d) 16-fluoroprostacyclin-11,15-diacetate methyl ester 3.0 ml of diazobicycloundecene are added to a solution of 1.17 g of the iodine ether prepared in Example (1c) in 10 ml of benzene and the mixture is stirred under argon for 3 hours. The mixture is then diluted with ether and the ether solution is extracted four times with water. The ether phases are dried over magnesium sulphate and concentrated in vacuo. 910 mg of the title compound are obtained in the form of an oil.

EXAMPLE 2

16-fluoro-7-oxoprostacyclin

A solution of 80 mg of the diacetate prepared in Example 1 is added to 6.0 ml of methanol and then, under argon, 0.45 ml of 1N sodium hydroxide solution is added. After 48 hours, the mixture is extensively concentrated in vacuo at room temperature and the residue is dissolved in 2.0 ml of water. The aqueous solution is extracted with ether, the ether phase is separated and the aqueous solution that remains is adjusted to pH 4.5 by the addition of 0.1N sulphuric acid solution. The aqueous phase is then extracted several times with ethyl acetate, and the combined ethyl acetate extracts are washed with water, dried over magnesium sulphate and concentrated. 62 mg of the title compound are obtained.

IR: 3400 (broad), 2950, 1740, 1715, 1660, 1460, 1360/cm.

EXAMPLE 3

11,15-bis(O-acetyl)-18,19-didehydro-19-methyl-7-oxoprostacyclin methyl ester

Analogously to Example 1, 141 mg of the title compound are obtained starting from 480 mg of 19-methyl-18,19-didehydroprostacyclin-11,15-diacetate methyl ester.

IR: 2950, 1750, 1710, 1670, 1440, 1370, 1240/cm.

The starting material for Example 3 is prepared as follows:

(3a) 4-bromo-2-methyl-2-butene (dimethylallyl bromide)

212 g of a 37% hydrogen bromide solution in glacial acetic acid are added at −15° C. to 65.6 g of freshly distilled isoprene. The reaction mixture is stored at −6° C. for 2 days and then poured into 1.5 l of ice water. The oil that separates is separated off and the aqueous phase is extracted three times with methylene chloride. The combined organic phases are dried over magnesium sulphate, concentrated in vacuo and then distilled. 87 g of the title compound are obtained: b.p. 41°–50° C. (30 mm).

(3b) 2-ethoxycarbonyl-5-methyl-4-hexenoic acid ethyl ester (dimethylallyl malonic acid diethyl ester)

11.5 g of sodium (cut up into small pieces) are placed in a three-necked flask having a reflux condenser, dropping funnel and stirrer. 250 ml of absolute ethanol are added dropwise so that the mixture boils briskly. 80 g of malonic acid diethyl ester and 76 g of the dimethylallyl bromide obtained according to Example (3a) are added dropwise in succession to the hot alcoholate solution. The mixture is maintained at boiling temperature under reflux for one hour. The sodium bromide that precipitates is then filtered off and the precipitate is washed with ether. The filtrate is washed with sodium chloride solution, the ether phase is separated, dried over sodium sulphate, concentrated in vacuo and distilled. 99 g of the title compound are obtained: b.p. 130°–132° C. (13 mm).

(3c) 2-carboxy-5-methyl-4-hexenoic acid (dimethylallylmalonic acid)

19.6 g of potassium hydroxide and 25 ml of water are added to a solution of 22.8 g of the diester obtained according to Example (3b) in 50 ml of ethanol and the mixture is heated under reflux for 4 hours. The solution is then extensively concentrated in vacuo, the residue is dissolved in 25 ml of water and the solution is acidified (pH 1) by the dropwise addition of concentrated hydrochloric acid while cooling with ice. The aqueous solution is extracted 5 times with ether, the combined ether phases are washed with saturated sodium chloride solution, dried over magnesium sulphate and concentrated in vacuo. The residue is recrystallised from benzene and 13.7 g of the title compound are obtained: m.p. 96°–97° C.

(3d) 5-methyl-4-hexenoic acid (dimethylallylacetic acid)

15 g of the dicarboxylic acid obtained according to Example (3c) are heated to 150°–160° C. in a distillation apparatus. When the evolution of carbon dioxide has ceased, the residue is distilled in vacuo. 10.1 g of the title compound are obtained: b.p. 102°–107° C. (10 mm).

(3e) 5-methyl-4-hexenoic acid methyl ester (dimethylallylacetic acid methyl ester)

An ethereal diazomethane solution is added to a solution of 13.1 g of the carboxylic acid obtained according to Example (3d) in 30 ml of ether until the yellow colour of the reaction solution remains constant. Excess diazomethane is removed by the dropwise addition of glacial acetic acid and the colourless solution is concentrated in vacuo. The residue is then distilled in vacuo. 10 g of the title compound are obtained: b.p. 59°–69° C. (13 mm).

(3f) (6-methyl-2-oxo-5-heptenylidene)-triphenylphosphorane 53 ml of n-butyllithium solution (2.2M) are added under argon to a suspension of 42.9 g of triphenylmethylphosphonium bromide in 400 ml of absolute ether and the solution is stirred at room temperature for 2 hours. Over a period of 1 hour, 8.2 g of the ester obtained according to Example (3e) in 100 ml of absolute ether are added drop-wise to the yellow solution of methylene triphenylphosphorane. After 1.5 hours, the white precipitate is filtered off and dissolved in water. The aqueous solution is extracted with ether and the ethereal extracts are combined with the filtrate. The combined ether solution is washed with saturated sodium chloride solution, dried over magnesium sulphate and concentrated in vacuo. For purification, the residue is filtered over silica gel in hexane/50-100% ethyl acetate. 12.34 g of the title compound are obtained.

(3g) (1S,5R, 6R,7R)-7-benzoyloxy-6-[(E)-7-methyl-3-oxo-1,6-octadienyl]-2-oxabicyclo[3.3.0]-octan-3-one A mixture of 3.9 g of (1S,5R,6R,7R)-6-formyl-7-benzoyloxy-2-oxabicyclo[3.3.0]octan-3-one [E. J. Corey et al., J. Am. Chem. Soc., 91, 5675 (1969)] and 5.5 g of the phosphorane prepared according to Example (3f) in 110 ml of absolute benzene is stirred at room temperature under argon for 5.5 hours. The reaction solution is then concentrated in vacuo and the residue is purified by column chromatography over silica gel in hexane/2-0-40% ethyl acetate. 3.8 g of the title compound are obtained.

(3h) (1S,5R,6R,7R,3'S)-7-benzoyloxy-6-[(E)-3-hydroxy-7-methyl-1,6-octadienyl]-2-oxabicyclo[3.3.0]octan-3-one 135 ml of ethereal zinc borohydride solution are added to a solution of 1.9 g of the ketone obtained in Example (3g) in 132 ml of dimethoxyethane and the mixture is stirred at room temperature under argon for 2.5 hours. The reaction solution is then diluted with 100 ml of ether and 10 ml of water are added dropwise. After 10 minutes, the ether solution is decanted off from the precipitate and the precipitate is washed repeatedly with ether. The combined ether phases are washed with water, dried over magnesium sulphate and concentrated in vacuo. A total of 4 such reactions are carried out. The combined crude products are purified by two-fold column chromatography on silica gel in methylene chloride/1-4% alcohol. 2.4 g of the title compound are obtained.

(3i) 2RS, 3aR,4R,5R,6aS,3'S)-4-[(E)-3-hydroxy-7-methyl-1,6-octadienyl]-5-hydroxyperhydrocyclopenta[b]furan-2-ol 4.5 ml of a 20% solution of diisobutylaluminium hydride in toluene are added dropwise under argon at −65° C. to a solution of 400 mg of the alcohol prepared according to Example (3h) in 16.5 ml of absolute toluene. After 30 minutes, 1.65 ml of isopropanol are added to the mixture and the temperature of the solution is allowed to rise to 0° C. 16.5 ml of water are then added to the solution and the whole is stirred for 10 minutes. The mixture is extracted three times with methylene chloride, the organic phases are combined, washed with saturated sodium chloride solution, dried over sodium sulphate and concentrated in vacuo. 353 mg of the title compound are obtained in the form of a colourless oil which is used in the next stage without further purification.

(3j) (5Z,13E)-(8R,9S,11R,12R,15S)-9,11,15-trihydroxy-19-methyl-5,13,18-prostatrienoic acid and (3k) the methyl ester thereof (3j) To a solution of 2.82 g of 4-carboxybutyltriphenylphosphonium bromide in 8 ml of absolute dimethyl sulphoxide there are added dropwise 12.2 ml of methanesulphinylmethyl sodium in absolute dimethyl sulphoxide (2.0 g of a 50% sodium hydride suspension are dissolved in 40 ml of absolute dimethyl sulphoxide over a period of half an hour at 70° C. under argon) and the mixture is stirred at room temperature under argon for 30 minutes. This solution is then added dropwise to a solution, cooled to 50° C., of 353 mg of the lactol obtained according to Example (3i) in 5 ml of absolute dimethyl sulphoxide and the mixture is stirred at 50° C. under argon for 3 hours. 40 ml of water are then added to the reaction solution and the mixture is extracted three times with ether. The organic extracts are discarded. The aqueous phase is acidified (pH 4) with a 10% citric acid solution and extracted, in succession, three times with a mixture of hexane/ether 1:1 and three times with pure methylene chloride. The combined organic phases are washed with saturated sodium chloride solution, dried over sodium sulphate and concentrated in vacuo. The residue is purified by chromatography on silica gel in ethyl acetate/methanol. 210 mg of the title compound are obtained.

(3k) The prostatrienoic acid obtained according to Example (3j) is dissolved in 2 ml of methylene chloride and an ethereal diazomethane solution is added. The solution is then concentrated in vacuo and the residue is purified by chromatography on silica gel with methylene chloride/1-8% ethanol as eluant. 180 mg of the title compound are obtained in the form of the methyl ester.

IR: 3390, 3000-2860, 1735, 1670, 1650, 1440, 1170, 1055, 1020/cm.

(3l) 5,6-dihydro-5-iodo-19-methyl-18,19-didehydroprostacyclin methyl ester

Analogously to Example (1b), 1.10 g of the title compound are obtained from 760 mg of the methyl ester prepared according to Example (3k).

(3m) 5,6-dihydro-5-iodo-19-methyl-18,19-didehydroprostacyclin-11,15-diacetate methyl ester Analogously to Example (1c), 1.20 g of the title compound are obtained starting from 1.10 g of the diol prepared according to Example (3l).

(3n) 18,19-didehydro-19-methylprostacyclin-11,15-diacetate methyl ester

Analogously to Example (1d), 915 mg of the title compound are obtained from 1.20 g of the diacetate prepared according to Example (3m).

Example 4

18,19-didehydro-19-methyl-7-oxoprostacyclin

A solution of 130 mg of 11,15-bis(O-acetyl)-18,19-didehydro-19-methyl-7-oxaprostacyclin methyl ester in 7.4 ml of methanolic potassium hydroxide solution (1.94 g of potassium hydroxide dissolved in 12.9 ml of water and 64.6 ml of methanol) is stirred at room temperature under argon for 3 hours. The reaction solution is then concentrated at room temperature in vacuo and 4 ml of water are added to the residue. The aqueous solution is extracted once with ether and the ether extract is discarded. The aqueous phase is acidified (pH 4.5-5.0) with a 10% citric acid solution and extracted, in succession, twice with chloroform, once with chloroform/10% ethanol and once with ethyl acetate. The organic extracts are combined, washed with saturated sodium chloride solution, dried over magnesium sulphate and concentrated. 96 mg of acid are obtained which, for purification, are chromatographed over silica gel in methylene chloride/30-40% acetone/3-9% ethanol. 85 mg of the title compound are obtained.

IR: 3400 (broad), 2940, 1740, 1710, 1665, 1440, 1370/cm.

Example 5

18,19-didehydro-19-methyl-7-oxoprostacyclin, tris(hydroxymethyl)-aminomethane salt

A solution of 38 mg of the acid described in Example 4 in 2.0 ml of acetonitrile is heated to 40° C. and a solution of 12 mg of tris(hydroxymethyl)-aminomethane in 0.1 ml of water is added. The mixture is stirred at room temperature for 14 hours. The excess solvent is then removed in vacuo and 86 mg of the title compound are obtained.

EXAMPLE 6

11,15-bis(O-2-tetrahydropyranyl)-19-chloro-18,19-didehydro-7-oxoprostacyclin methyl ester

Analogously to Example 1, 185 mg of the title compound are obtained starting from 500 mg of 18,19-didehydro-11,15-bis(tetrahydropyran-2-yloxy)-19-chloroprostacyclin methyl ester.

IR: 2950, 1740, 1710, 1660, 1440, 1370, 1050, 980/cm.

The starting material for Example 6 is prepared as follows:

(6a) 3-chloro-2-butenylmalonic acid ethyl ester 12.5 g of sodium (cut up into small pieces) are placed in a three-necked flask having a reflux condenser, a dropping funnel and a stirrer. 250 ml of absolute ethanol are added dropwise so that the mixture boils briskly. 80 g of distilled malonic acid diethyl ester are then added dropwise to the hot alcoholate solution. The solution is allowed to cool to approximately 75° C., and 66.5 g of cis-trans-1,3-dichloro-2-butene are added dropwise. The mixture is heated under reflux for 1 hour. The sodium chloride that precipitates is then filtered off and the precipitate is washed with methylene chloride. The organic solution is concentrated, the residue is dissolved in methylene chloride, and the solution is washed with saturated sodium chloride solution, dried over magnesium sulphate and concentrated in vacuo and distilled. 76 g of the title compound are obtained: b.p. 100°–108° C. (0.5 mm).

(6b) 3-chloro-2-butenylmalonic acid 19.4 g of potassium hydroxide are added to a solution of 24.87 g of the diester described in Example (6a) in 50 ml of ethanol and 25 ml of water and the mixture is heated under reflux for 35 hours. The solvent is then removed in vacuo, the residue is dissolved in 25 ml of water and, while cooling with ice, concentrated hydrochloric is added dropwise to the solution (pH 1). The aqueous phase is extracted 5 times using 100 ml of ether each time, the combined ether phases are washed with saturated sodium chloride solution, dried over sodium sulphate and concentrated in vacuo. The residue is recrystallised from benzene. 15.2 g of the title compound are obtained: m.p. 95°–97° C.

(6c) 5-chloro-4-hexenoic acid

In a distillation apparatus, 15 g of the dicarboxylic acid obtained in Example (6b) are decarboxylated analogously to Example (3d). The residue is distilled in vacuo and 10.8 g of the title compound are obtained: b.p. 129°–130° C. (13 mm).

(6d) 5-chloro-4-hexenoic acid methyl ester

A slight excess of ethereal diazomethane solution is added to a solution of 10.4 g of the carboxylic acid obtained in Example (6c). The reaction solution is concentrated in vacuo and then distilled. 10.4 g of the title compound are obtained: b.p. 87°–89° C. (18 mm).

(6e) 6-chloro-2-oxohept-5-enephosphonic acid dimethyl ester 21.8 ml of n-butyllithium solution (2.2M in hexane) are added dropwise at −65° C. to a solution of 5.58 g of methanephosphonic acid dimethyl ester in 160 ml of absolute tetrahydrofuran and the mixture is stirred at that temperature for 15 minutes. A solution of 4.05 g of the methyl ester obtained in Example (6d) in 10 ml of tetrahydrofuran is then added and the mixture is stirred at −65° C. for 1 hour. The solution is heated to −10° C., 2.80 ml of acetic acid are added and the mixture is concentrated. The residue is partitioned between ethene and water, the ether phase is separated, dried over magnesium sulphate and concentrated in vacuo. The residue is then purified by ball-tube distillation. 4.23 g of the title compound are obtained (bath temperature 180°–185° C., 1.5 torr).

(6f) (1S,5R,6R,7R)-6-[1E,6Z)-3-oxo-7-chloro-1,6-octadienyl]-7-benzoyloxy-2-oxabicyclo[3.3.0]octan-3-one To a suspension of 720 mg of sodium hydride (50% suspension in oil) in 85 ml of absolute dimethoxyethane there is added, dropwise at room temperature, a solution of 4.2 g of the phosphonate manufactured according to Example (6e) in 15 ml of dimethoxyethane and this mixture is stirred at room temperature under argon for 2 hours. A solution of 3.62 g of (1S,5R,6R,7R)-6-formyl-7-benzoyloxy-2-oxa-bicyclo[3.3.0]octan-3-one [J. Am. Chem. Soc., 96, 5865 (1974)] in 45 ml of dimethoxyethane is then added at −20° C. and the mixture is stirred at room temperature for a further 2 hours. The solution is then neutralised with acetic acid, diluted with ether and washed with 4% sodium bicarbonate solution. The ether phase is washed neutral with water, dried over magnesium sulphate and concentrated in vacuo. 3.80 g of the title compound are obtained in the form of an oil.

IR: 2950, 1770, 1720, 1700, 1640, 1460, 1280, 1160, 1115, 715/cm.

(6g) (1S,5R,6R,7R)-6-[(1E,6Z)-(3S)-3-hydroxy-7-chloro-1,6-octadienyl]-7-benzoyloxy-2-oxabicyclo[3.3.0]octan-3-one 235 ml of an ethereal zinc borohydride solution (manufacture: "Neuere Methoden der Präparativen Organischen Chemie, Vol. IV, page 241, Verlag Chemie) are added at 5° C. to a solution of 3.8 g of the ketone obtained according to Example (6f) in 230 ml of dimethoxyethane, and the mixture is stirred for 5 hours. After carefully adding water, the mixture is diluted with ether and the solution is shaken with brine. After separating the phases, the ether solution is dried over magnesium sulphate and concentrated in vacuo. The residue is chromatographed on silica gel in a mixture of pentane/ether (8:2). 2.1 g of the α-alcohol (3S-configuration) and then 930 mg of the corresponding β-alcohol (3R-configuration) are obtained.

IR (α-alcohol): 3600, 2965, 1770, 1720, 1600, 1270, 975/cm.

(6h) (1S,5R,6R,7R)-6-[(1E,6Z)-(3S)-3-hydroxy-7-chloro-1,6-octadienyl]-7-hydroxy-2-oxabicyclo[3.3.0]octan-3-one 640 mg of potassium bicarbonate are added to a solution of 2.1 g of the α-alcohol manufactured according to Example (6g) in 100 ml of methanol and the mixture is stirred at room temperature under argon for 4 hours. The solution is concentrated in vacuo, 90 ml of 1N hydrochloric acid are added and the mixture is extracted with ether. The ether extracts are washed neutral with water, dried over magnesium sulphate and concentrated in vacuo. After purification by column chromatography, 1.35 g of the title compound are obtained in the form of a colourless oil.

IR: 3600, 2965, 1770, 975/cm.

(6i) (1S,5R,6R,7R)-6-[(1E,6Z)-(3S)-3-(tetrahydropyran-2-yloxy)-7-chloro-1,6-octadienyl]-7-(tetrahydropyran-2-yloxy)-2-oxabicyclo[3.3.0]octan-3-one 756 mg of dihydropyrane and 5.5 mg of p-toluenesulphonic acid are added to a solution of 1.20 g of the diol prepared according to Example (6h) in 21 ml of methylene chloride and the mixture is stirred at 0° C. for 30 minutes. The mixture is then diluted with methylene chloride and extracted by shaking with a 4% sodium bicarbonate solution. The organic phase is washed with water, dried over magnesium sulphate and concentrated in vacuo. 1.85 mg of the title compound are obtained in the form of a colourless oil.

IR: 2950, 1768, 976/cm.

(6j) (2RS,3aR,4R,5R,6aS)-4-[(1E,6Z)-(3S)-3-(tetrahydropyran-2-yloxy)-7-chloro-1,6-octadienyl]-2-hydroxy-5-(tetrahydropyran-2-yloxy)-perhydrocyclopenta[b]furan Analogously to Example (3i), 1.79 g of the title compound are obtained from 1.85 g of the lactone prepared in Example (6i).

(6k) (5Z,13E,18Z)-(8R,9S,11R,12R,15S)-9-hydroxy-11,15-bis(tetrahydropyran-2-yloxy)-19-chloroprostatrienoic acid Analogously to Example (3j), 690 mg of the title prostatrienoic acid are obtained starting from 1.75 g of the lactol prepared in Example (6j).

(6l) the methyl ester of the title compound of Example (6k)

Analogously to Example (3k), 670 mg of the methyl ester are obtained starting from the prostatrienoic acid prepared in Example (6k).

(6m) 5-iodo-5,6-dihydro-18,19-didehydro-11,15-bis(-tetrahydropyran-2-yloxy)-19-chloroprostacyclin methyl ester 25.5 ml of water and 1.53 g of sodium bicarbonate are added to a solution of 670 mg of the methyl ester prepared in Example (6l) and the mixture is cooled to 0° C. A solution of 649 mg of iodine in 21 ml of ether are added dropwise to the cooled solution in the course of 10 minutes and the mixture is stirred at 0° C. for 4 hours. The aqueous phase is then separated from the ether solution and the ether phase is washed with 5% sodium thiosulphate solution. The organic phase is washed twice with water, dried over sodium sulphate and concentrated in vacuo. The residue is chromatographed over silica gel in hexane/11-20% ethyl acetate. 757 mg of the title compound are obtained.

IR: 2950, 1750, 1440, 1030, 980/cm.

(6n) 18,19-didehydro-11,15-bis(tetrahydropyran-2-yloxy)-19-chloroprostacyclin methyl ester 1.4 ml of diazabicycloundecene are added to a solution of 750 mg of the iodine ether described in Example (6m) in 7.0 ml of absolute benzene and the mixture is stirred at 50° C. under argon for 2 hours. The solution is then diluted with ether and washed five times with water. The organic phase is dried over magnesium sulphate and concentrated in vacuo. 602 mg of the title compound are obtained.

IR: 2950, 1750, 1705, 1440, 1370, 1050, 975/cm.

EXAMPLE 7

19-chloro-18,19-didehydro-7-oxoprostacyclin methyl ester

A solution of 480 mg of the bis-tetrahydropyranyl ether described in Example 6 in 20 ml of a mixture of glacial acetic acid/tetrahydrofuran/water (65:35:10) is stirred under argon for 15 hours. The solution is then diluted with ethyl acetate and washed, successively, with saturated sodium bicarbonate solution and water. The organic solution is dried over magnesium sulphate and concentrated in vacuo. The residue is chromatographed over silica gel in hexane/30-50% acetone. 292 mg of the title compound are obtained.

IR: 3450, 2950, 1740, 1710, 1660, 1440, 1370/cm.

EXAMPLE 8

19-chloro-18,19-didehydro-7-oxoprostacyclin

A solution of 200 mg of the diol prepared in Example 7 in 2.5 ml of methanolic potassium hydroxide solution (1.94 g of potassium hydroxide in 12.9 ml of water and 64.6 ml of methanol) is stirred at room temperature under argon for 3 hours. 10 ml of water are then added to the solution and the mixture is purified with ether. The ether phases are discarded. The aqueous phase is acidified (pH 4.5) with 10% citric acid solution and extracted, successively, twice with chloroform/5% ethanol and once with ethyl acetate. The organic phases are combined, washed with saturated sodium chloride solution, dried over sodium sulphate and concentrated in vacuo. 189 mg of the title compound are obtained.

IR: 3400 (broad), 2950, 1740, 1710, 1665, 1400, 1370/cm.

EXAMPLE 9

11,15-bis(O-2-tetrahydropyranyl)-18,19-tetradehydroprostacyclin methyl ester 130 mg of potassium tert.-butoxide are added to a solution of 581 mg of the prostacyclin derivative obtained according to Example (6n) in 3.5 ml of absolute dimethyl sulphoxide and the mixture is stirred at room temperature under argon for 3 hours. Ice is then added to the solution and the mixture is extracted with ether. The ether extract is washed with water, dried over magnesium sulphate and concentrated in vacuo. The residue (530 mg) can be used without further purification.

IR: 2950, 1750, 1705, 1440, 1370, 1050, 975/cm.

EXAMPLE 10

11,15-bis(O-2-tetrahydropyranyl)-18,19-tetradehydro-7-oxoprostacyclin methyl ester Analogously to Example 1, 115 mg of the title compound are obtained from 520 mg of the acetylene derivative prepared in Example 9.

IR: 2950, 1740, 1715, 1665, 1440, 1370, 1050, 975/cm.

EXAMPLE 11

7-oxo-18,19-tetradehydroprostacyclin methyl ester

Analogously to Example 7, 65 mg of the title compound are obtained from 110 mg of the 7-keto derivative prepared in Example 10.

IR: 3450, 2950, 1740, 1715, 1665, 1440, 1370/cm.

EXAMPLE 12

7-oxo-18,19-tetrahydroprostacyclin

Analogously to Example 8, 57 mg of the title compound are obtained from 65 mg of the methyl ester described in Example 11.

IR: 3400 (broad), 2950, 1740, 1710, 1665, 1440, 1370/cm.

EXAMPLE 13

11,15-bis(O-2-tetrahydropyranyl)-19-chloro-18,19-didehydro-16-methyl-7-oxoprostacyclin methyl ester Analogously to Example 1, 235 mg of the title compound are obtained from 650 mg of 16-methyl-18,19-didehydro-11,15-bis(tetrahydropyran-2-yloxy)-19-chloroprostacyclin methyl ester.

IR: 2950, 1740, 1710, 1670, 1440, 1370, 1050, 980/cm.

The starting material for Example 13 is prepared as follows:

(13a) 3-chloro-2-butenylmethylmalonic acid ethyl ester (2-ethoxycarbonyl-2-methyl-5-chloro-4-hexenoic acid ethyl ester)

Analogously to Example (6a), 85 g of the title compound, b.p. 105°–112° C. (0.5 mm), are obtained from 66.5 g of cis-trans-1,3-dichloro-2-butene and 87 g of methylmalonic acid diethyl ester.

(13b) 16-methyl-18,19-didehydro-11,15-bis(tetrahydropyran-2-yloxy)-19-chloroprostacyclin methyl ester Starting from the 3-chloro-2-butenylmethylmalonic acid ethyl ester prepared in Example (13a), 720 mg of the title compound are obtained analogously to Examples (6b)–(6n).

IR: 2950, 1750, 1705, 1440, 1370, 1050, 975/cm.

EXAMPLE 14

19-chloro-18,19-didehydro-16-methyl-7-oxoprostacyclin methyl ester

Analogously to Example 7, 305 mg of the title compound are obtained from 520 mg of the bis(tetrahydropyranyl) ether described in Example 13.

IR: 3450, 2950, 1750, 1710, 1660, 1440, 1370/cm.

EXAMPLE 15

19-chloro-18,19-didehydro-16-methyl-7-oxoprostacyclin

Analogously to Example 8, from 240 mg of the diol prepared in Example 14, 215 mg of the title compound are obtained.

IR: 3400 (broad), 2950, 1740, 1710, 1660, 1440, 1370/cm.

EXAMPLE 16

16-methyl-11,15-bis(tetrahydropyran-2-yloxy)-18,19-tetradehydroprostacyclin methyl ester Analogously to Example 9, 148 mg of the title compound are obtained from 590 mg of the 19-chloro derivative prepared in Example (13b).

IR: 2950, 1750, 1705, 1440, 1370, 1050, 975/cm.

EXAMPLE 17

11,15-bis(O-2-tetrahydropyranyl)-16-methyl-7-oxo-18,19-tetradehydroprostacyclin methyl ester Analogously to Example 1, 132 mg of the title compound are obtained from 490 mg of the acetylene derivative prepared in Example 16.

IR: 2950, 1740, 1715, 1660, 1440, 1370, 1050, 975/cm.

EXAMPLE 18

16-methyl-7-oxo-18,19-tetrahydroprostacyclin

Analogously to Examples 11 and 12, 63 mg of the title compound are obtained from 130 mg of the ketone prepared in Example 17.

IR: 3400 (broad), 2950, 1740, 1710, 1670, 1440, 1370/cm.

EXAMPLE 19

(17Z)-11,15-bis(O-acetyl)-17,18-didehydro-7-oxoprostacyclin methyl ester

Analogously to Example 1, 179 mg of the title compound are obtained from 480 mg of 17,18-(cis)-didehydroprostacyclin-11,15-diacetate methyl ester.

IR: 2950, 1740, 1710, 1660, 1460, 1360, 1240/cm.

The starting material for Example 19 is prepared as follows:

(19a) 17,18-(cis)-didehydroprostacyclin-11,15-diacetate methyl ester ($PGI_3$-11,15-diacetate methyl ester)

Analogously to Examples (1c) and (1d), 595 mg of the title compound are obtained from 750 mg of 5-iodo-17,18-(cis)-didehydro-$PGI_1$-methyl ester [R. Johnson et al., J. Am. Chem. Soc., 100, 7690 (1978)].

IR: 2950, 1740, 1700, 1460, 1360, 1240/cm.

EXAMPLE 20

(17Z)-17,18-didehydro-7-oxoprostacyclin

Analogously to Example 2, 105 mg of the title compound are obtained from 160 mg of the diacetate methyl ester described in Example 19.

IR: 3400 (broad), 2940, 1740, 1710, 1660, 1460, 1360/cm.

EXAMPLE 21

16-fluoro-7-oxoprostacyclin-methoxymethyl ester

A solution of 190 mg of the prostacyclin derivative prepared according to Example 2 is dissolved in 0.5 ml of absolute methylene chloride and, at 0° C., 0.1 ml of ethyl diisopropylamine and 0.06 ml of chloromethyl methyl ether are added. The solution is left to stand for 2 hours and then water is added to the mixture and the mixture is extracted several times with ethyl acetate. The organic extracts are combined, dried over magnesium sulphate and concentrated in vacuo. The residue is purified by preparative thin-layer chromatography (hexane/ethyl acetate 1:1) and 136 mg of the title compound are obtained in the form of an oil.

IR: 3450, 2950, 1740, 1710, 1660, 1460, 1360/cm.

EXAMPLE 22

16-methyl-11,15-bis(tetrahydropyran-2-yloxy)-18,19-tetradehydroprostacyclin methyl ester Analogously to Example (6n), 490 mg of the title compound are obtained starting from 630 mg of 16-methyl-11,15-bis(tetrahydropyran-2-yloxy)-5-iodo-5,6-dihydro-18,19-tetradehydroprostacyclin methyl ester.

IR: 2945, 1740, 1705, 1440, 1030/cm.

The starting material for Example 22 is prepared as follows:

(22a) 16-methyl-11,15-bis(tetrahydropyran-2-yloxy)-18,19-tetradehydroprostaglandin $F_{2\alpha}$ methyl ester An ethereal diazomethane solution is added to a solution of 546 mg of 16-methyl-11,15-bis(tetrahydropyran-2-yloxy)-18,19-tetradehydroprostaglandin F$_{2\alpha}$ (German Offenlegungsschrift 27 29 960) in 5.0 ml of ether until the yellow colour of the reaction solution remains constant. Excess diazomethane is removed by the dropwise addition of glacial acetic acid and the colourless reaction solution is concentrated in vacuo. The residue is chromatographed on silica gel by gradient elution in hexane/ethyl acetate. 523 mg of the title compound are obtained.

IR: 3045, 2940, 1740, 1440, 1030/cm.

(22b) 16-methyl-11,15-bis(tetrahydropyran-2-yloxy)-5-iodo-5,6-dihydro-18,19-tetradehydroprostacyclin methyl ester Analogously to Example (1b), 645 mg of the title compound are obtained from 520 mg of the methyl ester described in Example (22a).

IR: 2945, 1740, 1440, 1040/cm.

EXAMPLE 23

7-oxo-17,18-tetradehydro-11,15-bis(tetrahydropyran-2-yloxy)-prostacyclin methyl ester 210 mg of selenium dioxide are added to a solution of 530 mg of 11,15-bis(tetrahydropyran-2-yloxy)-17,18-tetradehydroprostacyclin methyl ester in 40 ml of dioxan and the mixture is heated at 95° C. under argon for 2 hours. The solution is stirred into ice-water and extracted several times with ether. The organic phases are combined, washed with semi-saturated sodium chloride solution, dried over magnesium sulphate and concentrated. The crude product (590 mg) is chromatographed on silica gel by gradient elution in hexane/20% ethyl acetate. Further separation is carried out by preparative thin-layer chromatography with a hexane/ethyl acetate mixture (85:15) as eluant. 145 mg of the title compound are obtained in the form of an oil.

IR: 2950, 1740, 1710, 1650, 1440, 1360, 1040/cm.

The starting material for Example 23 is manufactured as follows:

(23a) 3-hexynoic acid methyl ester

A solution of 5.9 g of 3-hexynoic acid in 50 ml of ether is treated with a slight excess of ethereal diazomethane solution. A few drops of glacial acetic acid are added to the mixture, the mixture is concentrated in vacuo and then distilled. 5.65 g of the title compound are obtained: b.p. 62° C. (5 mm).

IR: 2950, 2220, 1730, 1430, 1250, 1160, 1010/cm.

(23b) (2-oxo-4-heptynylidene)-triphenylphosphorane 61 ml of butyllithium solution (1.3M in hexane) are added dropwise, in the course of 20 minutes, to a suspension of 28.6 g of triphenylmethylphosphonium bromide in 300 ml of absolute ether and the mixture is stirred at room temperature for 2 hours. To this solution there is added dropwise, in the course of 0.5 hour, a solution of 5.04 g of the ester obtained in Example (23a) in 50 ml of absolute ether and the mixture is stirred at room temperature for 1.5 hours. The white precipitate is filtered off and washed with ether, the organic phase is washed with semi-saturated sodium chloride solution, dried over magnesium sulphate and concentrated. The crude product is purified over silica gel by gradient elution in hexane/ethyl acetate. 10.4 g of the title compound are obtained.

IR: 3080, 2940, 1590, 1400, 1120, 700/cm.

(23c) (1S,5R,6R,7R)-7-benzoyloxy-6-[(1E)-3-oxo-1-octen-5-ynyl]-2-oxabicyclo[3.3.0]octan-3-one A solution of 7.4 g of (1S,5R,6R,7R)-6-formyl-7-benzoyloxy-2-oxabicyclo[3.3.0]octan-3-one (E. J. Corey et al., J. Chem. Soc., 91, 5675 (1969)) and 10.3 g of the phosphorane prepared in Example (23b) in 200 ml of absolute toluene is stirred at room temperature for 5.5 hours. The reaction solution is concentrated in vacuo and the residue is chromatographed over silica gel by gradient elution in hexane/40% ethyl acetate. 9.7 g of the title compound are obtained.

IR: 3020, 1780, 1730, 1640, 1460, 1280, 1170, 1120, 1070, 975, 715/cm.

(23d) (1S,5R,6R,7R)-7-benzoyloxy-6-[(1E)-(3S)-3-hydroxy-1-octen-5-ynyl]-2-oxabicyclo[3.3.0]octan-3-one 5.81 g of sodium borohydride are introduced into a solution of 9.5 g of the ketone prepared in Example (23c) in 307 ml of absolute methanol cooled to $-40°$ C. and the mixture is stirred at that temperature for 3 hours. Excess sodium borohydride is then removed by adding 9.62 ml of glacial acetic acid and the mixture is concentrated to dryness at 30° C. in vacuo. Water is added to the residue and the solution is extracted several times with methylene chloride. The combined organic phases are washed with semi-saturated sodium chloride solution, dried over magnesium sulphate and concentrated. To separate the epimeric alcohols, the crude product (9.75 g) is carefully chromatographed on silica gel by gradient elution in pentane/ether. 4.4 g of the title compound are obtained.

IR: 3450, 3000, 2950, 1780, 1720, 1610, 1450, 1270, 1180, 1110, 1060, 980, 715/cm.

(23e) (1S,5R,6R,7R)-6-[(1E)-(3S)-3-hydroxy-1-octen-5-ynyl]-7-hydroxy-2-oxabicyclo[3.3.0]octan-3-one 712 mg of anhydrous potassium carbonate are introduced into a solution of 4.3 g of the alcohol prepared in Example (23d) in 47 ml of methanol and the mixture is stirred at room temperature for 3 hours. While cooling with ice, 0.72 ml of concentrated hydrochloric acid are then added dropwise to the reaction solution and the whole is concentrated in vacuo. The residue is dissolved in methylene chloride, the solution is dried over magnesium sulphate and concentrated in vacuo. The crude product is chromatographed over silica gel by gradient elution in methylene chloride/acetone. 2.85 g of the title compound are obtained.

IR: 3950, 2940, 1770, 1420, 1160, 1070, 1030, 970/cm.

(23f) (1S,5R,6R,7R)-6-[(1E)-(3S)-3-(tetrahydropyran-2-yloxy)-1-octen-5-ynyl]-7-(tetrahydropyran-2-yloxy)-2-oxabicyclo[3.3.0]-octan-3-one 1.0 ml of dihydropyran and 12.5 mg of p-toluenesulphonic acid are added to a solution of 2.80 g of the diol prepared in Example (23e) in 40 ml of absolute methylene chloride and the solution is stirred at room temperature for 45 minutes. The solution is diluted with methylene chloride and washed with semi-saturated sodium bicarbonate solution. The organic phases are then washed neutral with semi-saturated sodium chloride solution, dried over magnesium sulphate and concentrated. The crude product is chromatographed over silica gel by gradient elution in hexane/40% ethyl acetate. 4.42 g of the title compound are obtained.

IR: 2950, 1770, 1410, 1030/cm.

(23g) (2RS,3aR,4R,5R,6aS)-4-[(1E)-(3S)-3-(tetrahydropyran-2-yloxy)-1-octen-5-ynyl]-2-hydroxy-5-(tetrahydropyran-2-yloxy)-perhydrocyclopenta[b]furan 17.9 ml of a diisobutylaluminium hydride solution (20% in toluene) are added dropwise, under argon, to a solution of 4.3 g of the lactone prepared in Example (23f) in 84 ml of toluene cooled to −70° C. After 0.5 hour, 1.0 ml of isopropanol and 8.97 ml of water are added to the reaction mixture and the whole is stirred at room temperature for 2.5 hours. The precipitate is filtered off and washed with methylene chloride, and the combined organic phases are dried over magnesium sulphate and concentrated; 4.15 g of the title compound are obtained in the form of an oil.

IR: 3900, 2900, 1460, 1340, 1250, 1190, 1120, 1010, 970, 880/cm.

(23h) (5Z,13E)-(8R,9S,11R,12R,15S)-9-hydroxy-11,15-bis-(tetrahydropyran-2-yloxy)-17,18-tetradehydroprosta-5,13-dienoic acid and methyl ester 115 ml of a butyllithium solution (1.3M in hexane) are added under argon to a solution of 32.2 ml of hexamethyldisilazane in 92 ml of absolute tetrahydrofuran cooled to −12° C. and, while cooling, the resulting colourless solution of lithium hexamethyl silazide is added dropwise, in the course of 15 minutes, under argon, to a suspension of 34.0 g of carboxybutyltriphenylphosphonium bromide in 370 ml of absolute tetrahydrofuran. The suspension is stirred further at room temperature until a bright red solution is obtained (approx. 45 minutes). A solution of 4.0 g of the lactol prepared in Example (23g) in 270 ml of absolute tetrahydrofuran is then added dropwise to the phosphorane solution in the course of 10 minutes and the mixture is heated at 42°–45° C. under argon for 3 hours. When the reaction is complete, the mixture is stirred into 2 liters of 2.5% sodium chloride solution and acidified to a pH of 4.5–4.0 with a 10% citric acid solution. The aqueous suspension is extracted five times with 250 ml of ether each time and the combined ether phases are extracted four times with 40 ml of 2% sodium hydroxide solution each time. The aqueous sodium hydroxide extracts are acidified (pH 4.5) with a 10% citric acid solution and extracted four times with 100 ml of ether each time. These ether extracts are dried over magnesium sulphate and concentrated. 5.9 g of a crude product are obtained which is dissolved in 100 ml of methylene chloride and converted into the methyl ester by treatment with ethereal diazomethane solution. After complete reaction, the solution is concentrated in vacuo and the crude product is purified by chromatography over silica gel by gradient elution in hexane/20% ethyl acetate. 4.15 g of the title compound are obtained.

IR: 3950, 2900, 1730, 1430, 1120, 1020, 960/cm.

(23i) 5,6-dihydro-5-iodo-11,15-bis(tetrahydropyran-2-yloxy)-17,18-tetradehydroprostacyclin methyl ester 98 ml of water and 5.39 g of sodium bicarbonate are added to a solution of 4.1 g of the methyl ester obtained in Example 23h) in 91 ml of ether. The mixture is cooled to 4° C. and a solution of 4.11 g of iodine in 176 ml of ether is added under argon in the course of 20 minutes. After 4 hours, the reaction mixture is washed in a separating funnel, the aqueous phase is separated and the organic phase is washed with a 5% sodium thiosulphate solution. The colourless ether phase is washed with semi-saturated sodium chloride solution, dried over magnesium sulphate and concentrated in vacuo. 4.5 g of crude product are obtained which is chromatographed over silica gel by gradient elution in hexane/20% ethyl acetate. 4.28 g of the title compound are obtained.

IR: 2920, 1720, 1430, 1350, 1230, 1190, 1120, 1070, 1010, 960, 895, 860, 810, 730/cm.

(23j) 11,15-bis(tetrahydropyran-2-yloxy)-17,18-tetradehydroprostacyclin methyl ester 4.1 ml of diazobicycloundecene are added to a solution of 1.31 g of the iodine ether prepared in Example (23i) in 11.0 ml of absolute benzene and the solution is stirred at 50° C. for 2 hours. The solution is diluted with ethyl acetate and washed neutral with water. The organic extracts are dried over magnesium sulphate and concentrated in vacuo. 1.05 g of the title compound are obtained.

IR: 2900, 1730, 1680, 1430, 1350, 1230, 1130, 1020, 970/cm.

Example 24

7-oxo-17,18-tetradehydroprostacyclin methyl ester

A solution of 130 mg of the 7-oxo derivative prepared in Example (23) in 4.3 ml of a solvent mixture comprising acetic acid/water/tetrahydrofuran 65:35:10 is stirred at room temperature under argon for 17 hours. The reaction solution is carefully stirred into sodium bicarbonate solution and the aqueous phase is extracted three times with 50 ml of methylene chloride each time. The combined organic phases are washed neutral with semi-saturated sodium chloride solution, dried over magnesium sulphate and concentrated in vacuo. The residue (92 mg) is purified by preparative thin-layer chromatography in a chloroform/ethanol system (95:5) as eluant (eluted twice). 73 mg of the title compound are obtained.

IR: 3440, 2950, 1740, 1710, 1660, 1430, 1360/cm.

Example 25

7-oxo-17,18-tetradehydroprostacyclin

A solution of 60 mg of the methyl ester described in Example (24) in 1.2 ml of methanolic potassium hydroxide solution (1.94 g of potassium hydroxide in 12.9 ml of water and 64.6 ml of methanol) is stirred at room temperature under argon for 8 hours. The reaction solution is then diluted with 8 ml of water and extracted twice with ether. The aqueous phase is acidified (pH 4.5) with a 10% citric acid solution and extracted twice with ether and twice with ethyl acetate. The organic phases are combined, dried over magnesium sulphate and concentrated in vacuo. 52 mg of the title compound are obtained.

IR: 3400 (broad), 2950, 1740, 1710, 1660, 1440, 1370/cm.

What we claim is:

1. A 7-oxoprostacyclin derivative of the formula

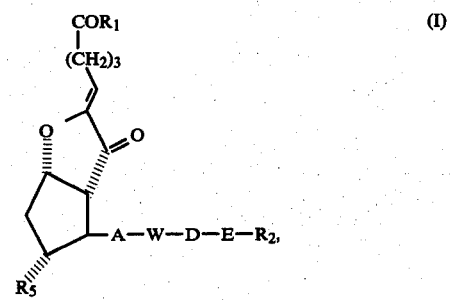

in which
R$_1$ represents the radical OR$_3$ wherein
R$_3$ represents a hydrogen atom, a heterocyclic, aryl, cycloalkyl or (C$_1$–C$_{10}$)alkyl radical said alkyl radical which is optionally substituted by one or more of the same or different substituents selected from halogen atoms and phenyl, (C₁–C₄)alkoxy and C₁–C₄-dialkylamino radicals, wherein the aryl radical contains 6–10 carbon atoms, wherein the cycloalkyl radical contains 4–10 carbon atoms and wherein the heterocyclic radical is aromatic and of 5- or 6-ring atoms containing a hetero atom which is O, N or S;

or the radical NHR₄ wherein

R₄ represents a hydrogen atom or a (C₁–C₁₀)alkanoyl or alkanesulphonyl radical,

A represents a —CH₂—CH₂—, cis—CH=CH— or trans—CH=CH— group,

W represents a

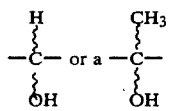

group in which, in each case, the OH group may be esterified by a benzoyl or (C₁–C₄)alkanoic acid radical or etherified by a tetrahydropyranyl, tetrahydrofuranyl, alkoxyalkyl or trialkylsilyl radical, and wherein the free or esterified hydroxy group may be in the α- or β-position, D and E together represent a direct bond, or D represents a straight-chain or branched-chain (C₁–C₅)alkylene radical, E represents an oxygen atom or a direct bond, R₂ represents a straight-chain or branched-chain (C₁–C₆)fluoroalkyl radical, a straight-chain or branched-chain (C₂–C₆)alkenyl radical which is optionally substituted by one or more of the same or different substituents selected from phenyl groups, halogen atoms and (C₁–C₄)alkyl radicals, and, if D and E together represent a direct bond, may also represent a (C₂–C₆)alkynyl radical which is optionally substituted in the 1-position by one or more halogen atoms or (C₁–C₄)alkyl radicals, R₅ represents a hydroxy group that may be esterified by a (C₁–C₄)alkanoic acid radical or etherified by a tetrahydropyranyl, tetrahydrofuranyl, alkoxyalkyl or trialkylsilyl radical.

2. A compound of claim 1, wherein R₂ represents a (C₁–C₆)fluoroalkyl radical or a (C₂–C₆)alkenyl radical which is unsubstituted or substituted by one or more of the same or different substituents which are phenyl radicals, halogen atoms or (C₁–C₄)alkyl radicals.

3. A compound of claim 1 wherein R₂ is alkynyl unsubstituted or substituted in the 1-position by one or more fluorine atoms or (C₁–C₄)alkyl radicals.

4. 11,15-bis(O-acetyl)-16-fluoro-7-oxoprostacyclin methyl ester a compound of the claim 1.

5. 16-fluoro-7-oxoprostacyclin a compound of claim 1.

6. 11,15-bis(O-acetyl)-18,19-didehydro-19-methyl-7-oxoprostacyclin methyl ester a compound of claim 1.

7. 18,19-didehydro-19-methyl-7-oxoprostacyclin a compound of claim 1.

8. 11,15-bis(O-2-tetrahydropyranyl)-19-chloro-18,19-didehydro-7-oxoprostacyclin methyl ester a compound of claim 1.

9. 19-chloro-18,19-didehydro-7-oxoprostacyclin methyl ester a compound of claim 1.

10. 19-chloro-18,19-didehydro-7-oxoprostacyclin a compound of claim 1.

11. 11,15-bis(O-2-tetrahydropyranyl)-18,19-tetradehydro-7-oxoprostacyclin methyl ester a compound of claim 1.

12. 7-oxo-18,19-tetradehydroprostacyclin methyl ester a compound of claim 1.

13. 7-oxo-18,19-tetradehydroprostacyclin a compound of claim 1.

14. 11,15-bis(O-2-tetrahydropyranyl)-19-chloro-18,19-didehydro-16-methyl-7-oxoprostacyclin methyl ester a compound of claim 1.

15. 19-chloro-18,19-didehydro-16-methyl-7-oxoprostacyclin methyl ester a compound of claim 1.

16. 19-chloro-18,19-didehydro-16-methyl-7-oxoprostacyclin a compound of claim 1.

17. 11,15-bis(O-2-tetrahydropyranyl)-16-methyl-7-oxo-18,19-tetradehydroprostacyclin methyl ester a compound of claim 1.

18. 16-methyl-7-oxo-18,19-tetradehydroprostacyclin a compound of claim 1.

19. (17Z)-11,15-bis(O-acetyl)-17,18-didehydro-7-oxoprostacyclin methyl ester a compound of claim 1.

20. (17Z)-17,18-didehydro-7-oxoprostacyclin a compound of claim 1.

21. 16-fluoro-7-oxoprostacyclin methoxymethyl ester a compound of claim 1.

22. 11,15-bis(O-2-tetrahydropyranyl)-7-oxo-17,18-tetradehydroprostacyclin methyl ester a compound of claim 1.

23. 7-oxo-17,18-tetradehydroprostacyclin methyl ester a compound of claim 1.

24. 7-oxo-17,18-tetradehydroprostacyclin a compound of claim 1.

25. A physiologically tolerable salt of a compound of claim 1 wherein R₃ represents a hydrogen atom.

26. 18,19-didehydro-19-methyl-7-oxoprostacyclin tris(hydroxymethyl)-aminomethane salt a compound of claim 1.

27. A pharmaceutical preparation which comprises a hypotensive or bronchodilatory effective amount of a compound of claim 1 or a physiologically tolerable salt thereof, in admixture or conjunction with a pharmaceutically suitable carrier.

28. A pharmaceutical preparation of claim 27, which is in unit dosage form.

29. A method of treating a human or animal body which comprises administering a hypotensive or bronchodilatory effective amount of a compound of claim 1 or a physiologically tolerable salt thereof or a pharmaceutical preparation containing said compound in a dosage range from 1 to 1500 μg/kg/day to a human or an animal.

* * * * *